(12) United States Patent
Trieu et al.

(10) Patent No.: US 7,229,441 B2
(45) Date of Patent: Jun. 12, 2007

(54) FLEXIBLE SYSTEMS FOR SPINAL STABILIZATION AND FIXATION

(75) Inventors: Hai Trieu, Cordova, TN (US); Jon Serbousek, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 477 days.

(21) Appl. No.: 10/083,199

(22) Filed: Feb. 26, 2002

(65) Prior Publication Data
US 2002/0120270 A1    Aug. 29, 2002

Related U.S. Application Data

(60) Provisional application No. 60/272,114, filed on Feb. 28, 2001.

(51) Int. Cl.
*A61B 17/56* (2006.01)
*A61B 17/58* (2006.01)

(52) U.S. Cl. .................................... 606/61
(58) Field of Classification Search ............... 606/61, 606/69, 70, 71, 60, 72, 73, 232; 623/17.11
See application file for complete search history.

(56) References Cited

U.S. PATENT DOCUMENTS

| | | | |
|---|---|---|---|
| 3,463,158 A | 8/1969 | Schmitt et al. | |
| 3,710,789 A | 1/1973 | Ersek | |
| 4,401,112 A * | 8/1983 | Rezaian .................. | 606/61 |
| 4,570,623 A | 2/1986 | Ellison et al. | |
| 4,610,688 A | 9/1986 | Silvestrini et al. | |
| 4,665,951 A | 5/1987 | Ellis | |
| 4,728,329 A | 3/1988 | Mansat | |
| 4,743,260 A | 5/1988 | Burton | |
| 4,755,183 A | 7/1988 | Kenna | |
| 4,772,287 A | 9/1988 | Ray et al. | |
| 4,790,303 A * | 12/1988 | Steffee .................... | 606/61 |
| 4,820,305 A | 4/1989 | Harms et al. | |
| 4,828,562 A * | 5/1989 | Kenna .................. | 623/13.13 |
| 4,834,755 A | 5/1989 | Silvestrini et al. | |
| 4,883,486 A | 11/1989 | Kapadia et al. | |
| 4,904,260 A | 2/1990 | Ray et al. | |

(Continued)

FOREIGN PATENT DOCUMENTS

EP     0304305     2/1989

(Continued)

OTHER PUBLICATIONS

Anterior Cruciate Ligament (ACL) Reconstruction Technique, Patellar Tendon Graft, Orthopaedic Associates of Portland, Sports Medicine Center, www.orthoassociates.com/acltech.htm, Douglas W. Brown, M.D., pp. 1-9, Sep. 27, 2000.

(Continued)

*Primary Examiner*—Pedro Philogene
(74) *Attorney, Agent, or Firm*—Krieg DeVault LLP

(57) ABSTRACT

Systems for spinal stabilization and fixation replace, reconstruct or augment the spinal ligamentous and/or bony tissues resected during surgical procedures. The spinal stabilization system includes at least an implant configured to span the intervertebral disc space with at least one of its ends attached to a respective vertebral body by at least one anchor. The system has a low profile conformable to the spinal anatomy.

58 Claims, 11 Drawing Sheets

U.S. PATENT DOCUMENTS

| | | | |
|---|---|---|---|
| 4,917,700 A | | 4/1990 | Aikins |
| 4,955,911 A | | 9/1990 | Frey et al. |
| 5,011,484 A | | 4/1991 | Bréard |
| 5,084,051 A | | 1/1992 | Törmälä et al. |
| 5,102,421 A | | 4/1992 | Anspach, Jr. |
| 5,108,395 A | | 4/1992 | Laurain |
| 5,108,397 A | * | 4/1992 | White .......................... 606/60 |
| 5,156,616 A | | 10/1992 | Meadows et al. |
| 5,157,111 A | | 10/1992 | Pachence |
| 5,171,273 A | | 12/1992 | Silver et al. |
| 5,180,393 A | | 1/1993 | Commarmond |
| 5,222,987 A | | 6/1993 | Jones |
| 5,344,421 A | | 9/1994 | Crook |
| 5,346,492 A | | 9/1994 | Morgan |
| 5,376,188 A | | 12/1994 | Kaplan et al. |
| 5,380,328 A | | 1/1995 | Morgan |
| 5,395,372 A | * | 3/1995 | Holt et al. ..................... 606/61 |
| 5,397,359 A | | 3/1995 | Mittelmeier et al. |
| 5,443,483 A | | 8/1995 | Kirsch |
| 5,456,722 A | | 10/1995 | McLeod et al. |
| 5,496,372 A | | 3/1996 | Hamamoto et al. |
| 5,527,311 A | | 6/1996 | Procter et al. |
| 5,540,964 A | | 7/1996 | Mallen |
| 5,549,679 A | | 8/1996 | Kuslich |
| 5,591,235 A | | 1/1997 | Kuslich |
| 5,609,634 A | | 3/1997 | Voydeville |
| 5,611,801 A | * | 3/1997 | Songer .......................... 606/73 |
| 5,634,944 A | | 6/1997 | Magram |
| 5,674,295 A | | 10/1997 | Ray et al. |
| 5,681,310 A | | 10/1997 | Yuan et al. |
| 5,711,960 A | | 1/1998 | Shikinami |
| 5,721,049 A | | 2/1998 | Marcolongo et al. |
| 5,824,093 A | | 10/1998 | Ray et al. |
| 5,906,828 A | | 5/1999 | Cima et al. |
| 5,989,256 A | * | 11/1999 | Kuslich et al. ............... 606/74 |
| 6,022,376 A | | 2/2000 | Assell et al. |
| 6,031,148 A | | 2/2000 | Hayes et al. |
| 6,045,554 A | | 4/2000 | Grooms et al. |
| 6,077,076 A | | 6/2000 | Comfort |
| 6,086,589 A | | 7/2000 | Kuslich et al. |
| 6,093,205 A | | 7/2000 | McLeod et al. |
| 6,113,640 A | | 9/2000 | Törmälä et al. |
| 6,120,503 A | * | 9/2000 | Michelson .................... 606/61 |
| 6,121,172 A | | 9/2000 | Marcolongo et al. |
| 6,143,036 A | | 11/2000 | Comfort |
| 6,156,037 A | * | 12/2000 | LeHuec et al. ............... 606/61 |
| 6,162,537 A | | 12/2000 | Martin et al. |
| 6,293,949 B1 | * | 9/2001 | Justis et al. .................... 606/61 |
| 6,332,894 B1 | | 12/2001 | Stalcup et al. |
| 6,361,538 B1 | * | 3/2002 | Fenaroli et al. .............. 606/73 |
| 6,368,326 B1 | * | 4/2002 | Dakin et al. ................. 606/103 |
| 6,607,530 B1 | * | 8/2003 | Carl et al. ..................... 606/61 |

FOREIGN PATENT DOCUMENTS

| | | |
|---|---|---|
| EP | 0353936 | 2/1990 |
| EP | 0507162 | 4/1991 |
| FR | 2612392 | 3/1987 |
| FR | 2 709 410 A1 | 3/1995 |
| NL | C 1009471 | 12/1999 |
| WO | WO 98/55053 | 12/1998 |
| WO | WO 99/47082 | 9/1999 |
| WO | WO 99/62439 | 12/1999 |
| WO | WO 00/64365 | 11/2000 |
| WO | WO 00/67651 | 11/2000 |

OTHER PUBLICATIONS

Anterior Cruciate Ligament (ACL) Graft Options, Orthopaedic Associates of Portland, Sports Medicine Center, www.orthoassociates.com/ACL_grafts.htm, F. Lincoln Avery, M.D., pp. 1-10, Sep. 27, 2000.

Graft Choices in ACL Reconstruction, Carleton Sports Medicine Clinic, www.carletonsportsmed.com/graftacl.htm, pp. 1-6, Sep. 27, 2000.

PCL Reconstruction: Fixation Techniques; ,*Wheeless' Textbook of Orthopaedics*; www.medmedia.com/o12/5000.htm, Sep. 27, 2000 p. 1 of 1.

Arthrotek Product Information, www.arthrotek.com and product literature; Sep. 27, 2000.

* cited by examiner

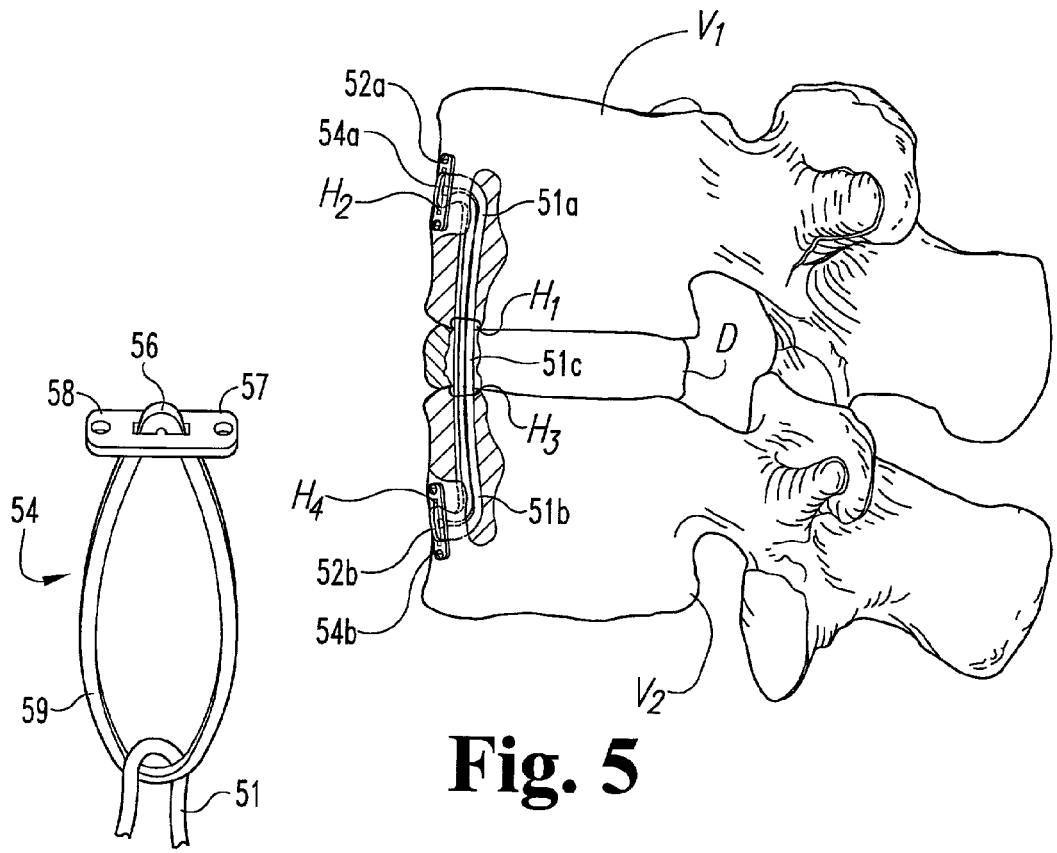
Fig. 5
Fig. 7
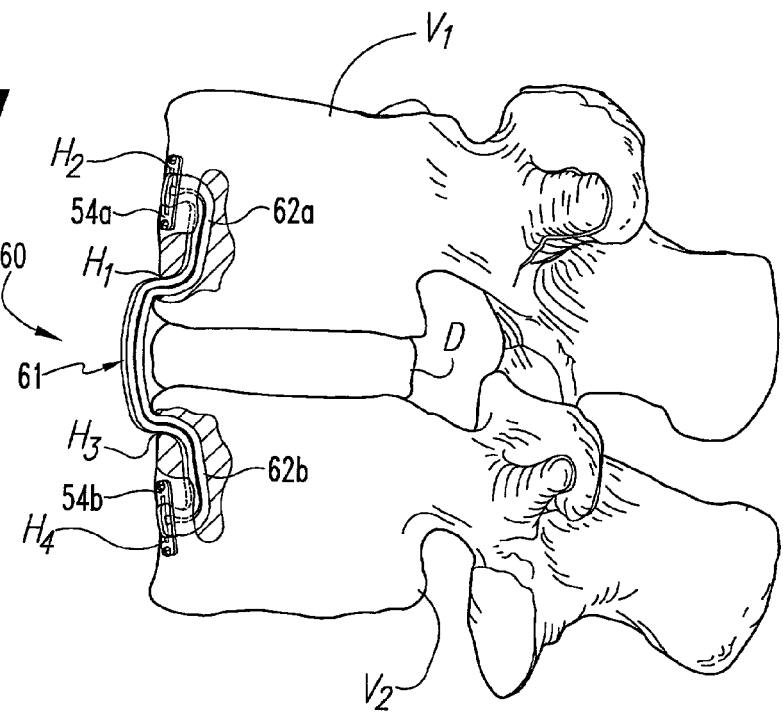
Fig. 6

FLEXIBLE SYSTEMS FOR SPINAL STABILIZATION AND FIXATION

CROSS-REFERENCE TO RELATED APPLICATION

This application claims the benefit of the filing date of Provisional Patent Application No. 60/272,114 filed on Feb. 28, 2001.

BACKGROUND

The present invention is directed devices and methods for use in spinal surgery, and more particularly to devices and methods for stabilizing the spine.

Various spinal surgical procedures require access of a subject disc space or vertebral body, such as for the repair of a herniated disc or vertebral body, the insertion of one or more interbody fusion devices, interbody spacers, or artificial discs. In order to access a spinal column, one or more spinal ligaments and bony tissue may have to be severed or at least partially resected to allow insertion of devices and/or surgical instruments into or to the disc space or vertebral body. It also may be desirable to augment or replace existing spinal ligaments and bony tissue. Posterior or anterior rigid metal constructs can also be used to stabilize the spinal column after these techniques are completed.

Rigid metal plates or rods on the anterior, antero-lateral, lateral or posterior portions of the spinal column segment are in close contact with and exposed to the adjacent vasculature and tissue. It is desirable that the potential for screw back out, loosening, bending of the construct, and stress shielding be reduced or eliminated in view of this close contact with the vasculature and the surrounding tissue.

SUMMARY OF THE INVENTION

The present invention is directed systems and methods for spinal stabilization and fixation. The systems are useful in the replacement, reconstruction or augmentation of spinal ligamentous or bony tissues, and also in resisting the tensile and rotational loading applied thereto by spinal motion.

In one form, the spinal stabilization systems include at least an elongated implant configured to span the intervertebral disc space with its ends attached to a respective vertebral body. The ends of the implant can be placed in tunnels formed in the adjacent vertebrae. The implant can have a substantially flexible yet substantially inelastic body with a low profile capable of conforming to the spinal anatomy. The anchors used to attach the ends of the implant to the vertebrae can be at least partially concealed in the vertebral body to which it is engaged, further reducing the profile of the device. Examples of suitable anchors include interference screws, suture anchors, bone screws, buttons, pin fasteners, and staples. It is further contemplated that the implant and anchors can be made from nonresorbable or resorbable material.

In one technique, the stabilization system can be attached to and stabilize the anterior portion of the spinal column. The stabilization system can also be attached to and stabilize the lateral or antero-lateral portion of the spinal column. In another technique, the stabilization system is attached to a posterior portion of the spinal column via anchors engaged to the vertebrae at any one of a number of locations, including but not limited to the facets, pedicles, pars, transverse processes, or spinous processes.

There are also various methods for securing a flexible implant to adjacent vertebral bodies in which the anchor and at least a portion of the implant is placed in a tunnel formed in the vertebral body. The attachment techniques provide a low profile system that reduces exposure and contact with the adjacent anatomic structures.

These and other forms, aspects, embodiments, features and advantages of the present invention will be apparent from the following description of the illustrated embodiments.

BRIEF DESCRIPTION OF THE FIGURES

FIG. 5 is a side elevational view in partial section of a spinal column segment having another embodiment spine stabilization system attached thereto.

FIG. 6 is a side elevational view in partial section of a spinal column segment having a further embodiment spine stabilization system attached thereto.

FIG. 7 is a perspective view of one embodiment of an anchor for attaching spine stabilization systems to vertebral bodies.

DESCRIPTION OF THE ILLUSTRATED EMBODIMENTS

Figure 1:
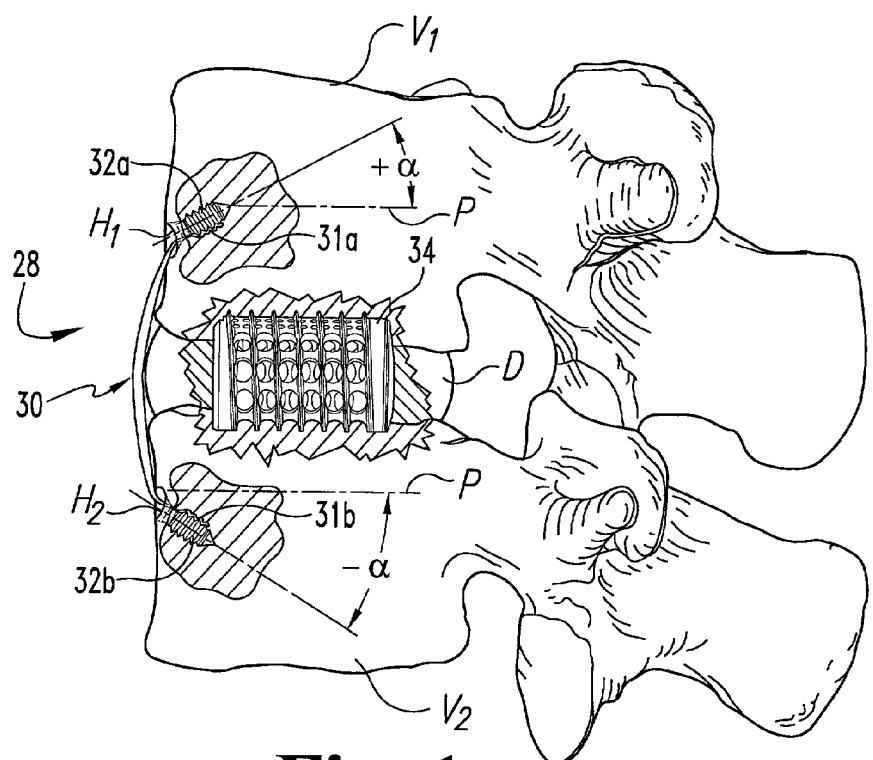
FIG. 1 is a side elevational view in partial section of a spinal column segment having an interbody fusion device inserted into the disc space and one embodiment spine stabilization system attached to the vertebral bodies.

For the purposes of promoting an understanding of the principles of the invention, reference will now be made to the illustrated embodiments and specific language will be used to describe the same. It will nevertheless be understood that no limitation of the scope of the invention is thereby intended. Any such alterations and further modifications of the invention, and any such further applications of the principles of the invention as illustrated herein are contemplated as would normally occur to one skilled in the art to which the invention relates.

The present invention includes spine stabilization systems in which flexible implants are anchored to the adjacent vertebrae. The stabilization systems have application in stabilizing the anterior, antero-lateral, lateral and/or posterior portions of a spinal column segment including one or more vertebral levels. The implants have a low profile and are conformable to the spinal anatomy to minimize intrusion into the surrounding tissue and vasculature. The implants attach to vertebrae and prevent separation of the vertebrae while allowing normal extension and articulation of the spinal column segment. Portions of the implants and the anchors attaching the implant to vertebrae can be at least partially or fully embedded within the vertebrae to minimize intrusion into the surrounding tissue and vasculature.

It is contemplated that the implants of the spine stabilization systems described herein can be made from resorbable material, nonresorbable material and combinations thereof. In one example, resorbable implants can be used with interbody fusion devices since a permanent exterior stabilization may not be desired after fusion of the vertebrae. It is also contemplated that the anchors used to attach the implants to the vertebrae can be made from resorbable material, nonresorbable material, and combinations thereof.

The implants can be flexible, tear resistant, and/or suturable. The implant can be fabricated from synthetic flexible materials in the form of fabrics, non-woven structures, two or three dimensional woven structures, braided structures, and chained structures. The implants can also be fabricated from natural/biological materials, such as autograft or allograft, taken from patellar bone-tendon-bone, hamstring tendons, quadriceps tendons, or Achilles tendons, for example. Growth factors or cells can be incorporated into the implant for bone ingrowth and bony attachment or for soft tissue ingrowth. Possible growth factors that can be incorporated include transforming growth factor β1, insulin-like growth factor 1, platelet-derived growth factor, fibroblast growth factor, bone morphogenetic protein, LIM mineralization protein (LMP), and combinations thereof.

Possible implant materials include synthetic resorbable materials such as polylactide, polyglycolide, tyrosine-derived polycarbonate, polyanhydride, polyorthoester, polyphosphazene, calcium phosphate, hydroxyapatite, bioactive glass and combinations thereof. Possible implant materials also include natural resorbable materials such as autograft, allograft, xenograft, soft tissues, connective tissues, demineralized bone matrix, and combinations thereof. Possible implant material further include nonresorbable materials such as polyethylene, polyester, polyvinyl alcohol, polyacrylonitrile, polyamide, polytetrafluorethylene, poly-paraphenylene terephthalamide, cellulose, shape-memory alloys, titanium, titanium alloys, stainless steel, and combinations thereof.

The spine stabilization systems described herein include anchors to attach the implant to the vertebrae. It is contemplated the anchors can be, for example, interference screws or anchors, gull anchors, suture anchors, pin fasteners, bone screws with spiked washers, staples, and buttons. It is contemplated that the anchors can be made from resorbable materials, nonresorbable materials, and combinations thereof. Possible synthetic resorbable materials include polylactide, polyglycolide, tyrosine-derived polycarbonate, polyanhydride, polyorthoester, polyphosphazene, calcium phosphate, hydroxyapatite, bioactive glass, and combinations thereof. Possible natural resorbable materials include cortical bone, autograft, allograft, and xenograft. Possible nonresorbable materials include carbon-reinforced polymer composites, shape-memory alloys, titanium, titanium alloys, cobalt chrome alloys, stainless steel, and combinations thereof.

Referring now to FIG. 1, there is shown a spine stabilization system attached to vertebrae V1 and V2. Stabilization system 28 includes a flexible implant 30 that extends along the anterior faces of vertebrae V1 and V2, and is attached to first vertebra V1 and the second vertebra V2. A fusion device 34 has been inserted into disc space D for fusion of vertebra V1 and vertebra V2. Implant 30 can resist extension, flexion, and/or lateral bending loads created by motion of the spinal column depending on the location or locations of the spinal column segment on which the implant is positioned.

Flexible implant 30 has a first end 31a and an opposite second end 31b. Vertebra V1 includes a first opening H1 in its anterior face and a first tunnel extending therefrom. Vertebra V2 has a second opening H2 in its anterior face and a second tunnel extending therefrom. The ends 31a and 31b are inserted into respective ones of the first and second tunnels through openings H1 and H2. An anchor 32a is inserted through opening H1 and into the tunnel of vertebra V1 to secure end 31a to vertebrae V1. Similarly, an anchor 32b is inserted through opening H2 and into the tunnel of vertebra V2 to secure end 31b to vertebrae V2. Anchors 32a, 32b are illustrated as threaded interference screws that are embedded into vertebral bodies V1 and V2 so that they do not protrude from the anterior faces of vertebrae V1 and V2. However, as with the other implants discussed herein, other anchors and anchoring techniques described herein could also be employed with implant 30.

Figure 3:
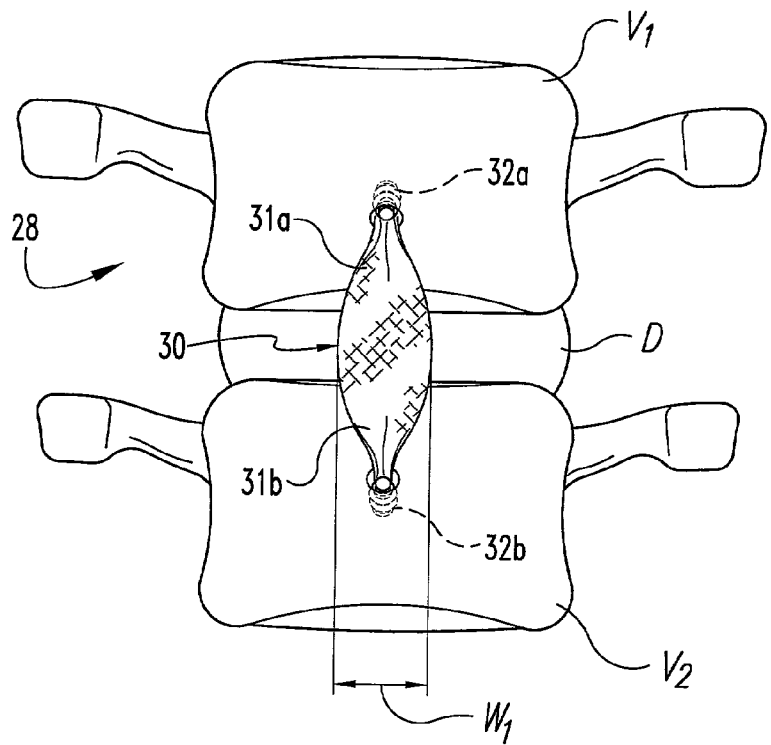
FIG. 3 is an anterior elevational view of a spinal column segment having another embodiment spine stabilization system attached thereto.

Interference anchors 32a, 32b can be oriented at an angle ±α with respect to the axial plane P of spinal column that provides a smooth transition for implant 30 as it enters openings H1 and H2 of vertebrae V1 and V2. This reduces stress concentrations at the junction between the implant and the vertebrae. In one embodiment, angle α is about 45 degrees. Other embodiments contemplate angular orientations that range from 0 degrees to about 80 degrees and from about 25 degrees to 65 degrees. As shown in FIG. 3, implant 30 has a reduced lateral width W1 that minimizes the lateral intrusion of implant 30 into the surrounding tissue.

The ends of implant 30 and the other implants described herein can be provided with pigtails or other extensions of reduced size for insertion through the openings and tunnels formed in the vertebrae. It is also contemplated that the ends of the implant can include eyelets, holes, loops or other configuration suitable for engagement with an anchor.

Figure 2:
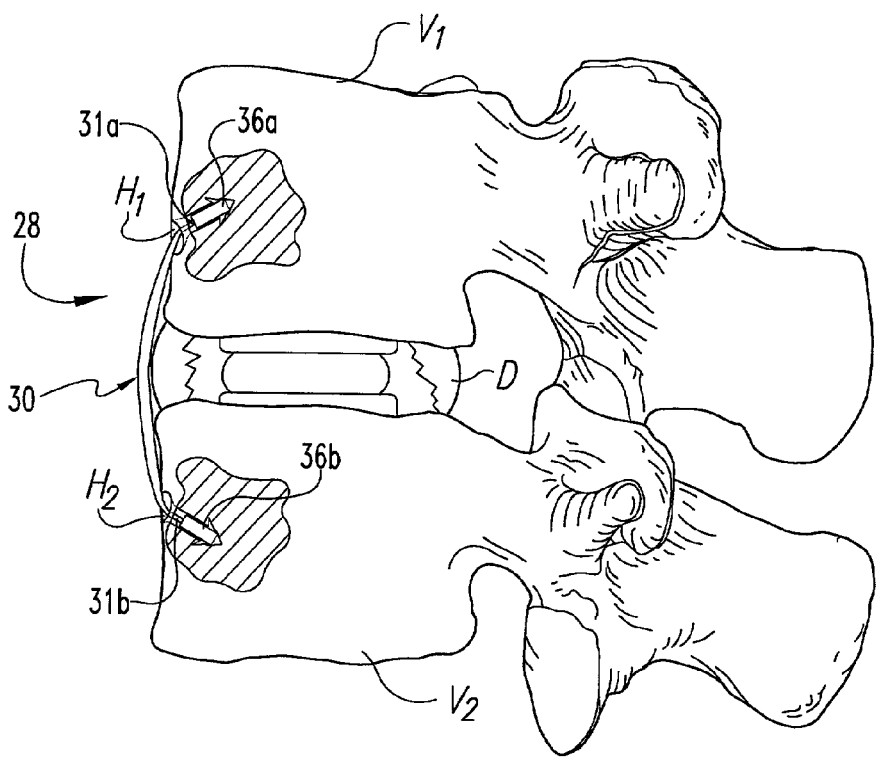
FIG. 2 is a side elevational view in partial section of a spinal column segment having an artificial disc inserted into the disc space and another embodiment spine stabilization system attached to the vertebral bodies.

Referring now to FIG. 2, a spine stabilization system 28' similar to system 28 includes an implant 30 with opposite ends 31a and 31b attached to vertebra V1 and V2, respectively. An artificial disc 38 is placed in disc space D. Implant ends 31a and 31b are attached to gull anchors 36a and 36b, respectively. Gull anchors 36a, 36b are placed through respective ones of openings H1 and H2 and embedded in tunnels formed in vertebrae V1 and V2, respectively, along with the corresponding ends 31a, 31b of implant 30. Gull anchors 36a, 36b have wings that are pivotable toward their shaft of the anchor during insertion and are pivotable laterally away from the anchor shaft to resist pullout of the anchor from vertebra after insertion therein.

Figure 4:
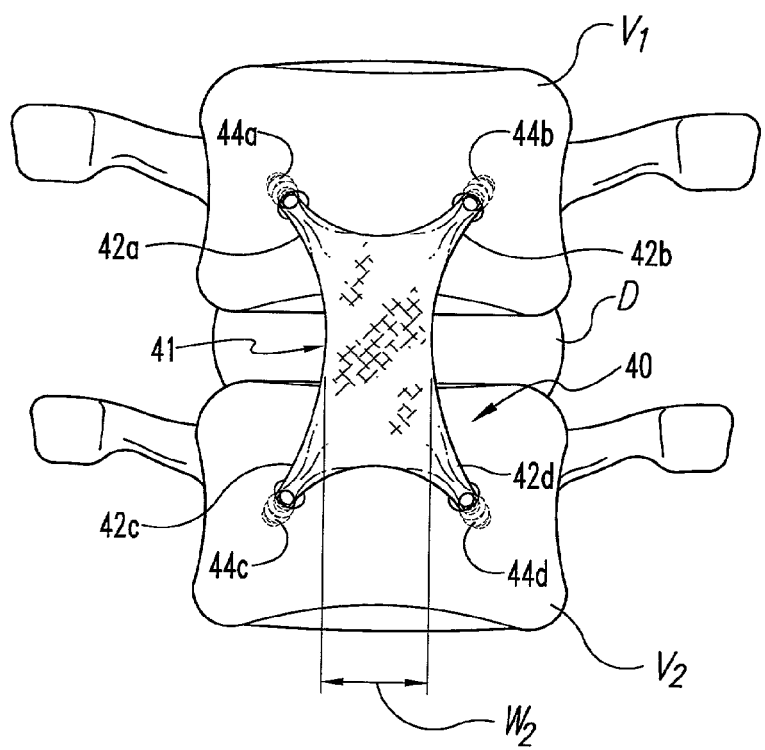
FIG. 4 is an anterior view of a spinal column segment having a further embodiment spine stabilization system attached thereto.

Referring now to FIG. 4, another embodiment spine stabilization system 40 is illustrated attached to vertebrae V1 and V2. System 40 includes an implant 41 attached along the anterior faces of vertebrae V1 and V2. Implant 41 has a width W2 for attachment of two anchors to each end of implant 41. The width W2 also provides greater coverage of the annulus tissue surrounding disc space D. Anchors 44a and 44b are attached to corners 42a and 42b, respectively, of implant 41 to secure it to vertebra V1. Anchors 44c and 44d are attached to corners 42c and 42d, respectively, of implant 41 to secure it to vertebra V2.

Referring now to FIGS. 5–7 there are shown two additional embodiments of a spinal stabilization system attached to vertebrae V1 and V2. In FIG. 5 stabilization system 50 includes an implant 51 extending along the anterior faces of vertebrae V1 and V2. Implant 51 has a first end 52a attached to vertebra V1 and an opposite second 52b attached to vertebra V2. Opening H1 opens adjacent to or through the vertebral endplate of vertebra V1, and a first tunnel extends therefrom in vertebra V1 to opening H2 at its anterior face. First end 52a of implant 51 is placed into opening H1 and through the tunnel and attached to vertebra V1 with anchor 54a at opening H2. A second tunnel is formed in vertebra V2 between opening H3 adjacent to or through the vertebral endplate of vertebra V2 and opening H4 at its anterior face. Second end 52b of implant 51 is placed into opening H3 and through the second tunnel and attached to vertebra V2 with anchor 54b at opening H4.

In one embodiment, anchor 54 is a button or flange member that is secured to the ends of implant 51 and abuts against the anterior face of the respective vertebra. As shown in FIG. 7, anchor 54 has a bearing member 56 with a first flange 57 and an opposite second flange 58. Flanges 57, 58 are sized larger than openings H2, H4 and abut against the face of the vertebra around the respective opening in order to secure implant 51 to the vertebra.

In one embodiment, attachment loop 59 is attached to bearing member 56 to secure implant 51 thereto. Attachment loop 59 can extend into the tunnel adjacent the respective opening H2, H4. Implant 51 can be looped around attachment loop 59 as shown in FIG. 7, or attachment loop 59 can extend through the body of implant 51 like a suture. It is contemplated that attachment loop 59 can be, for example, a tether, cable, or wire. In another embodiment, not attachment loop is provided, but rather the ends of implant 51 extend through openings or slots provided in respective ones of the anchors 54a, 54b and are secured thereto by tying, knotting, looping or otherwise fixing the ends of implant 51 to the adjacent anchor 54a, 54b.

In FIG. 6 stabilization system 60 includes an implant 61 having a first end 62a attached to vertebra V1 and an opposite second 62b attached to vertebra V2. A first tunnel is formed in vertebra V1 between opening H1 at the lower portion of the anterior face of vertebra V1 and opening H2 at the upper portion of the anterior face of vertebra V1. First end 62a of implant 61 is placed into opening H1 and through the tunnel for attachment to vertebra V1 with anchor 54a at opening H2. A second tunnel is formed in vertebra V2 between opening H3 at the upper portion of the anterior face of vertebra V2 and opening H4 at the lower portion of the anterior face of vertebra V2. Second end 62b of implant 61 is placed into opening H3 and through the second tunnel for attachment to vertebra V2 with anchor 54b at opening H4.

It is contemplated that implants 51, 61 or other implants described herein can be provided in multiple segments, of which each segment is attached to a respective one of the vertebrae V1 and V2. The multiple implant segments can be attached to one another adjacent disc space D by suturing, stapling, fusing or otherwise securing the ends of the implant segments together to form a single implant 51, 61. For example, implant 51 includes an upper segment 51a attachable to vertebra V1 and a lower segment 51b attachable to vertebra V2. Upper segment 51a is attached to lower segment 51b at overlap region 51c.

Figure 8:
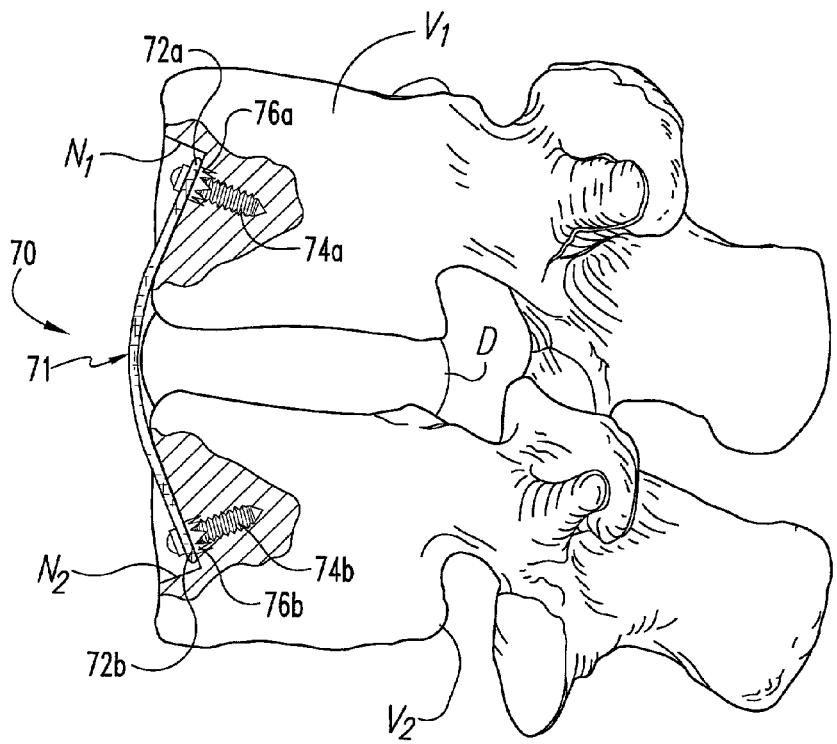
FIG. 8 is a side elevational view in partial section of a spinal column segment having another embodiment spine stabilization system attached thereto.

Referring now to FIG. 8 another embodiment spine stabilization system 70 is attached to vertebrae V1 and V2. System 70 has an implant 71 that extends between vertebrae V1 and V2. Implant 71 has opposite ends 72a and 72b that are positioned in notches N1 and N2 formed in the anterior faces of vertebrae V1 and V2, respectively. Implant 71 has first end 72a attached to vertebra V1 via first anchor 74a in notch N1. Notch N1 is formed in vertebra V1 to recess the head of anchor 74a below the anterior face of vertebra V1, minimize or eliminating its protrusion into the adjacent tissue. Anchor 74a is illustrated in the form of a threaded screw that extends through a spiked washer 76a. The screw and spikes of washer 76a extend through end 72a of implant 71 and into vertebra V1.

Implant 71 has opposite second end 72b attached to vertebra V2 via second anchor 74b in notch N2. Notch N2 is formed in vertebra V2 to recess the head of anchor 74b below the anterior face of vertebra V2, minimizing or eliminating its protrusion into the adjacent tissue. Anchor 74b is illustrated in the form of a threaded screw that extends through a spiked washer 76b. The screw and spikes of washer 76b extend through end 72b and into vertebra V2.

Figure 9:
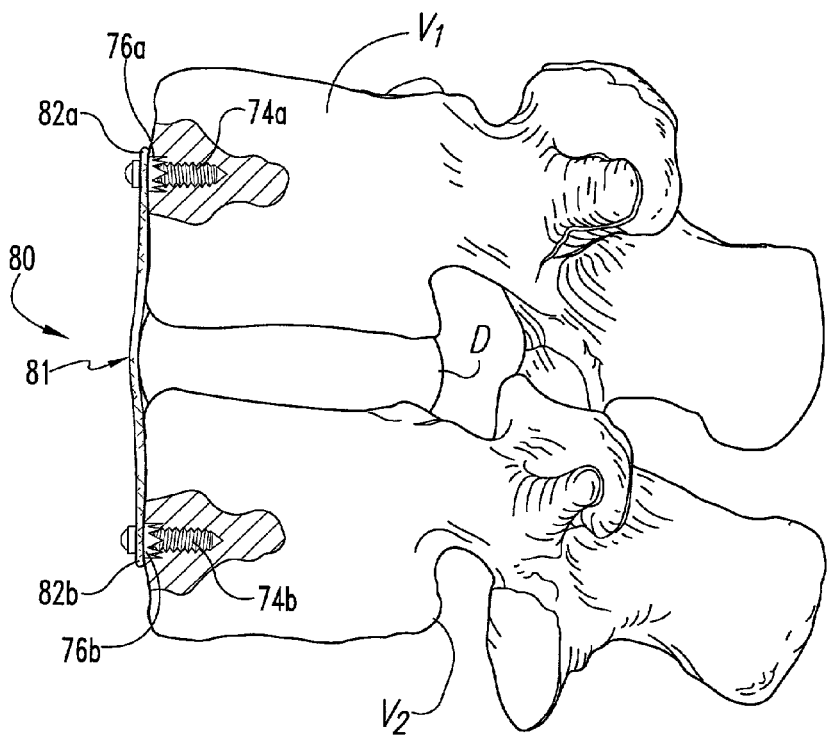
FIG. 9 is a side elevational view in partial section of a spinal column segment having another embodiment spine stabilization system attached thereto.

Referring now to FIG. 9 another embodiment spine stabilization system 80 is attached to vertebrae V1 and V2 with anchors 74a, 74b. Anchors 74a, 74b include spiked washers 76a, 76b and a bone screw extending therethrough such as discussed above. System 80 has an implant 81 that extends along and is conformable to the anterior faces of vertebrae V1 and V2. Implant 81 has a first end 82a attached to vertebra V1 via first anchor 74a. The screw and spikes of washer 76a extend through end 82a and into vertebra V1 with the head of anchor 74a abutting against the anterior face of vertebra V1. Implant 81 has an opposite second end 82b attached to vertebra V2 via second anchor 74b. The screw and spikes of washer 76b extend through end 82b and into vertebra V2 with the head of anchor 74b abutting against washer 76b.

In one form, it is contemplated that the surface of washers 76a, 76b in contact with the head of the screw extending therethrough is concave to at least partially receive the screw head so that the profile of the screw head above washer 76a is minimized. In another form, the spiked washers are in the form of staples configured to attach the ends of the implant to the vertebrae without a bone screw.

Figure 10:
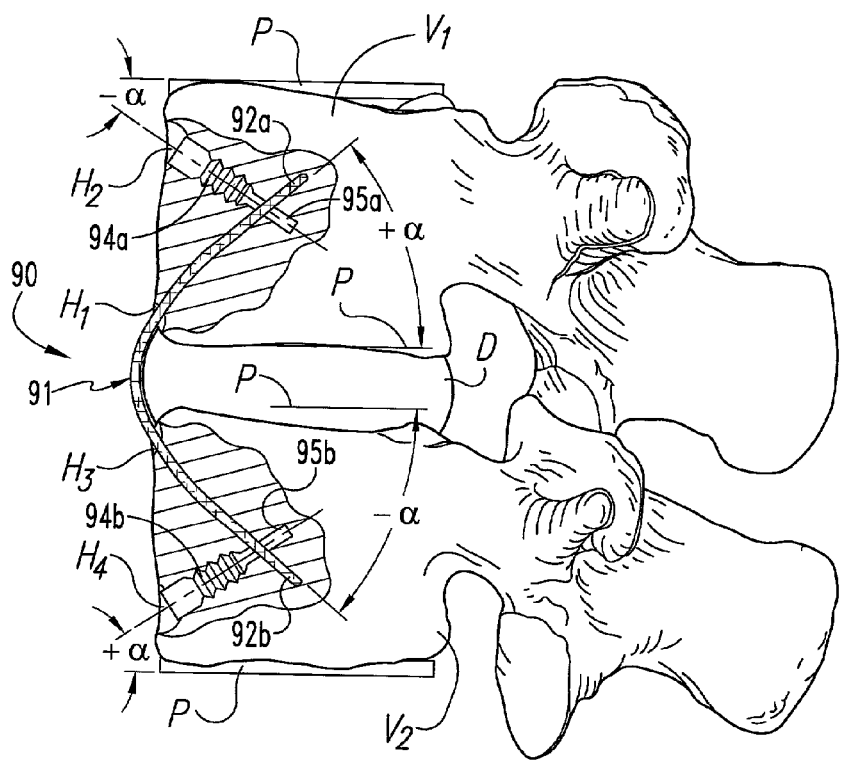
FIG. 10 is a side elevational view in partial section of a spinal column segment having another embodiment spine stabilization system attached thereto.

Referring now to FIG. 10, another embodiment spine stabilization system 90 is shown attached to the anterior faces of vertebrae V1 and V2. System 90 has an implant 91 having a first end 92a and an opposite second end 92b embedded in vertebrae V1 and V2, respectively. Vertebra V1 has a first opening H1 and a first tunnel extending therefrom into vertebra V1 at an angle +α relative to axial plane P of the spinal column. A second opening H2 having a second tunnel extending therefrom is formed into vertebra V1 at an angle +α relative to axial plane P so that the second tunnel intersects the first tunnel extending from opening H1. First end 92a is positioned through first opening H1 and into the first tunnel where it is attached to vertebra V1 by a first anchor 94a.

Anchors 94a, 94b are illustrated in the form of a pin fastener having a screw thread portion with a pin 95a extending therefrom. Anchor 94a is threaded into opening H2 so that pin 95a extends through second end 92a to secure implant 91 to vertebra V1. The end of anchor 94a opposite pin 95a is provided without a head so that anchor 95a can be recessed below the anterior face of vertebra V1.

Vertebra V2 has a third opening H3 and a third tunnel extending therefrom at an angle -α into vertebra V2. A fourth opening H4 having a fourth tunnel extending therefrom at an angle +α is formed in vertebra V2 so that the fourth tunnel intersects the third tunnel extending from third opening H3. Second end 92b of implant 91 is positioned through third opening H3 and into the third tunnel where it is attached to vertebra V2 by a second anchor 94b. Anchor 94b has a screw thread with a pin 95b extending therefrom. Anchor 94b is threaded into opening H4 so that pin 95b extends through second end 92b to secure implant 91 to vertebra V2. The end of anchor 94b opposite pin 95b is provided without a head so that anchor 95b can be recessed below the outer surface of vertebra V2.

Figure 11:
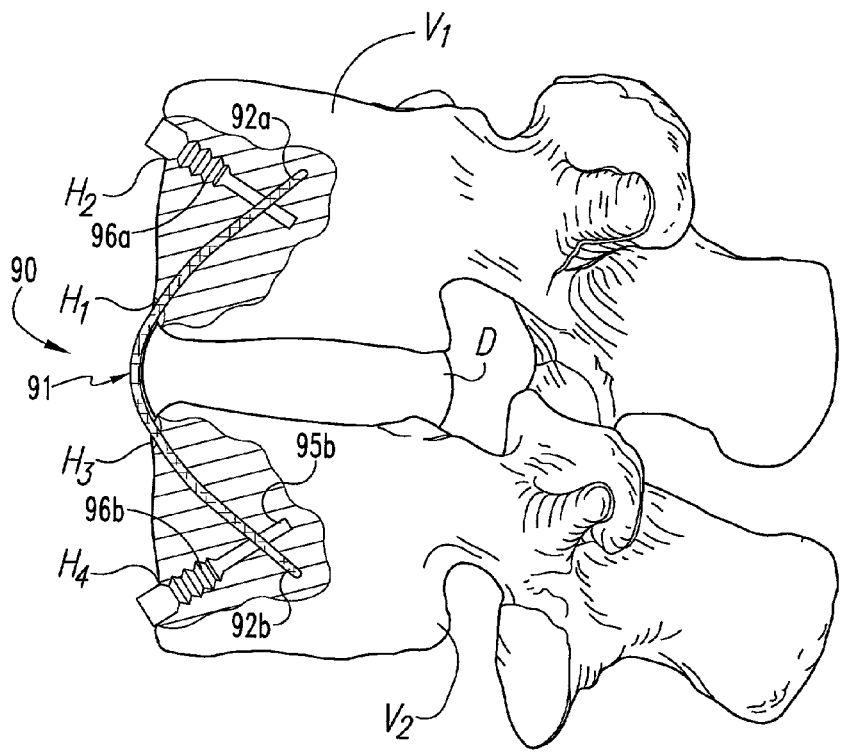
FIG. 11 is a side elevational view in partial section of a spinal column segment having another embodiment spine stabilization system attached thereto.

Referring now to FIG. 11, implant 90 is shown with a slightly altered anchoring arrangement as compared to that of FIG. 10. The anchors 96a, 96b of FIG. 11 are illustrated in the form of a pin fastener having an exposed head that extends slightly from the anterior face of vertebra V1 and V2, respectively.

It is contemplated that the implant 91 of FIGS. 10 and 11 can be provided with eyelet or other opening at each end 92a, 92b sized to receive the pin extending distally from the screw thread portion of anchors 94, 96. It is also contemplated that the pins of anchors 94, 96 can extend directly through the implant material at its ends 92a, 92b.

Figure 12:
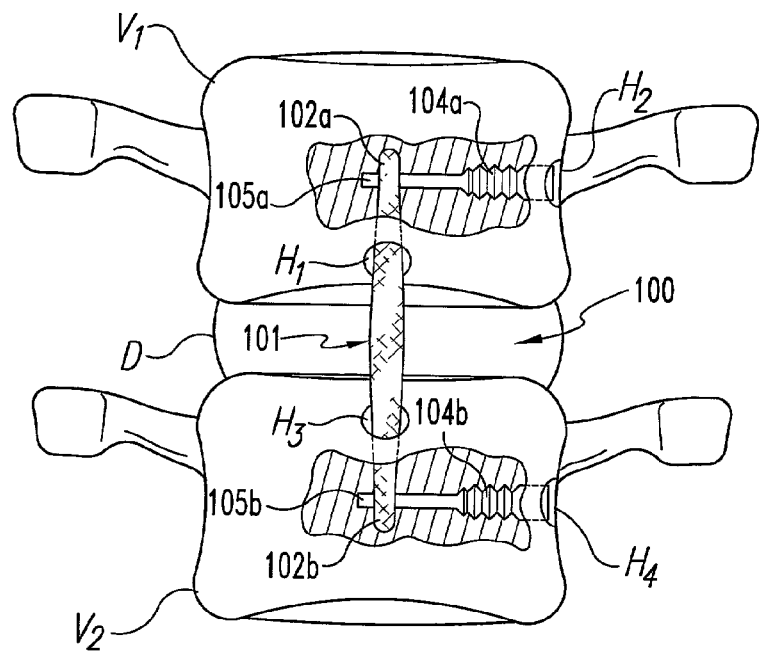
FIG. 12 is an anterior elevational view in partial section of a spinal column segment having another embodiment spine stabilization system attached thereto.

Referring now to FIG. 12, there is illustrated spine stabilization system 100 attached along the anterior faces of vertebrae V1 and V2. System 100 has an implant 101 with a first end 102a and opposite second end 102b. A first tunnel extends from first opening H1 posteriorly into vertebra V1, and second tunnel extends laterally from a second opening H2 formed in the lateral side of vertebra V1 and intersects the first tunnel. First end 102a extends through opening H1 and into the first tunnel. Anchors 104a, 104b are illustrated in the form of a pin fastener. A first anchor 104a has a screw thread portion with a pin 105a extending therefrom. First anchor 104a is placed through second opening H2 so that pin 105a engages first end 102a of implant 101.

A third tunnel extends from third opening H3 posteriorly into vertebra V2, and a fourth tunnel extends laterally from a fourth opening H4 formed in the lateral side of vertebra V2 and intersects the third tunnel. Second end 102b extends through opening H3 and into the third tunnel. A second anchor 104b has a screw thread portion with a pin 105b extending therefrom. Second anchor 104b is placed through fourth opening H4 so that pin 105b engages first end 102b of implant 101.

Figure 13:
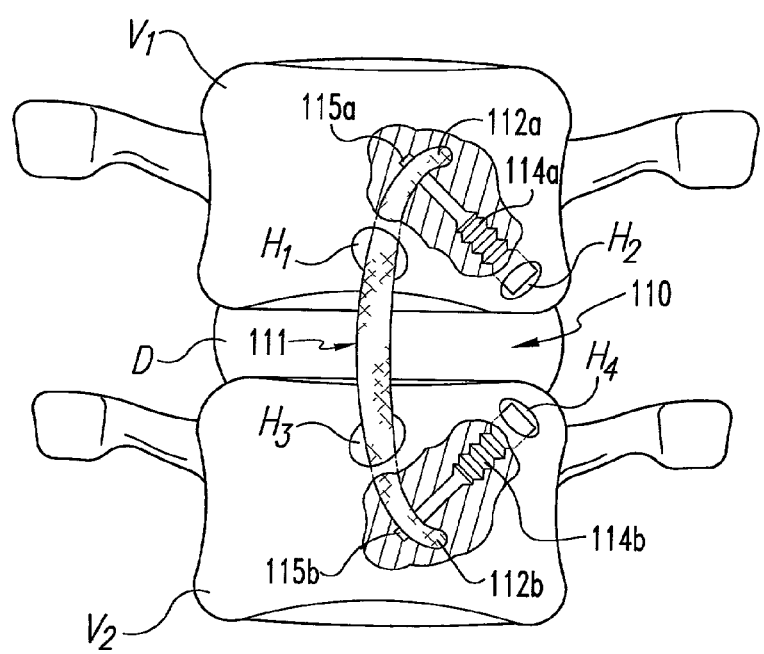
FIG. 13 is an anterior elevational view in partial section of a spinal column segment having another embodiment spine stabilization system attached thereto.

Referring now to FIG. 13, there is illustrated another embodiment spine stabilization system 110 extending along the anterior faces of vertebrae V1, V2 and having an obliquely oriented attachment arrangement in each of the vertebrae V1, V2. System 110 includes an implant 111 extending between a first end 112a and a second end 112b. First opening H1 is formed in the anterior face of vertebra V1 and has a first tunnel extending therefrom that curves obliquely relative to the sagittal plane toward the lateral face of vertebra V1. A second opening H2 is formed in the antero-lateral face of vertebra V1 and has a second tunnel extending therefrom that intersects the first tunnel. Implant 111 has a first end 112a extending through first opening H1 into the first tunnel. A first anchor 114a has a screw thread portion with a pin 115a extending therefrom. Anchor 114a is placed through opening H2 so that pin 115a engages first end 112a of implant 111.

Third opening H3 is formed in the anterior face of vertebra V2 and has a first tunnel extending therefrom that curves obliquely relative to the sagittal plane toward the lateral face of vertebra V2. A fourth opening H4 is formed in the antero-lateral face of vertebra V2 and has a fourth tunnel extending therefrom that intersects the third tunnel. Implant 111 has a second end 112b extending through third opening H3. A second anchor 114b has a screw thread portion with a pin 115b extending therefrom. Anchor 114b is placed through opening H4 so that pin 115b engages first end 112b of implant 111.

Figure 14:
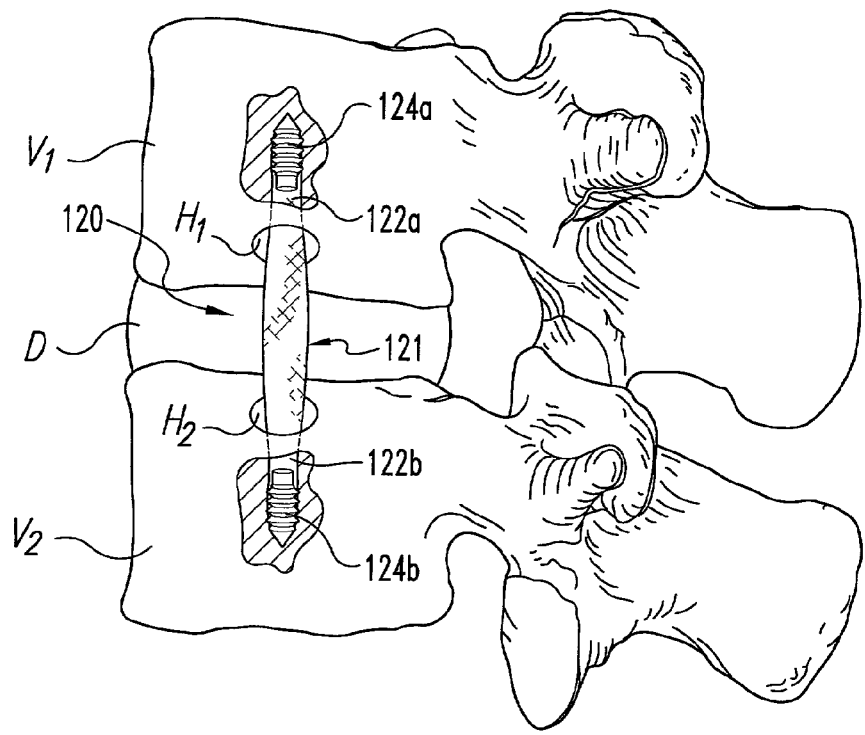
FIG. 14 is a side elevational view in partial section of a spinal column segment having another embodiment spine stabilization system attached thereto.

Referring now to FIG. 14 another embodiment spine stabilization system 120 is attached to vertebrae V1 and V2. System 120 has an implant 121 extending along the lateral faces of vertebrae V1 and V2. Vertebra V1 has a first opening H1 in the lateral face of vertebra V1 and a first tunnel extending therefrom. First end 122a extends through first opening H1 and into the first tunnel where anchor 124a secures implant 121 to vertebra V1. Vertebra V2 has a second opening H2 in the lateral face of vertebra V2 and a second tunnel extending therefrom. Second end 122b extends through opening H2 and into the second tunnel where second anchor 124b secures implant 121 to vertebra V2. Anchors 124a, 124b are interference screws embedded in the respective vertebrae V1, V2 and in engagement with respective ones of the ends of implant 121.

Figure 15:
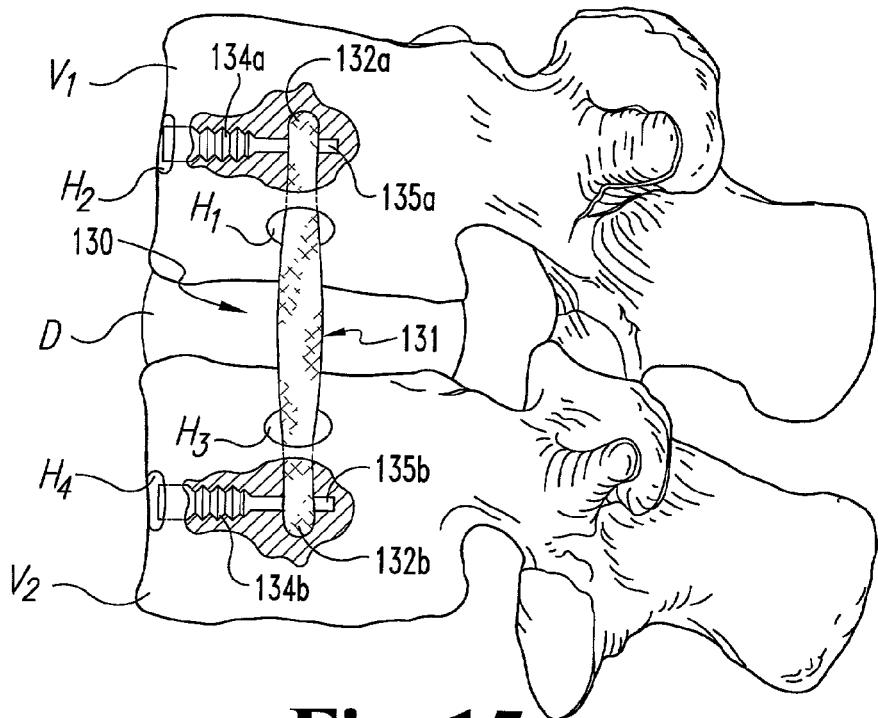
FIG. 15 is a side elevational view in partial section of a spinal column segment having another embodiment spine stabilization system attached thereto.

Referring now to FIG. 15, there is illustrated another embodiment spine stabilization system 130 having an implant 131 extending along the lateral faces of vertebrae V1 and V2. First opening H1 is formed in the lateral face of vertebra V1 and has a first tunnel extending into vertebra V1. A second opening H2 is formed in the anterior face of vertebra V1 and has a second tunnel extending therefrom that intersects the first tunnel. Implant 131 has a first end 132a extending through first opening H1 and into the first tunnel. A first anchor 134a in the second tunnel has a screw thread portion with a pin 135a extending therefrom that engages first end 132a of implant 131.

Third opening H3 is formed in the lateral face of vertebra V2 and has a third tunnel extending therefrom into vertebra V2. A fourth opening H4 is formed in the anterior face of vertebra V2 and has a fourth tunnel extending therefrom that intersects the third tunnel. Implant 131 has a second end 132b extending through third opening H3 into the third tunnel. A second anchor 134b in the fourth tunnel has a screw thread portion with a pin 135b extending therefrom that engages second end 132b of implant 131.

Figure 16:
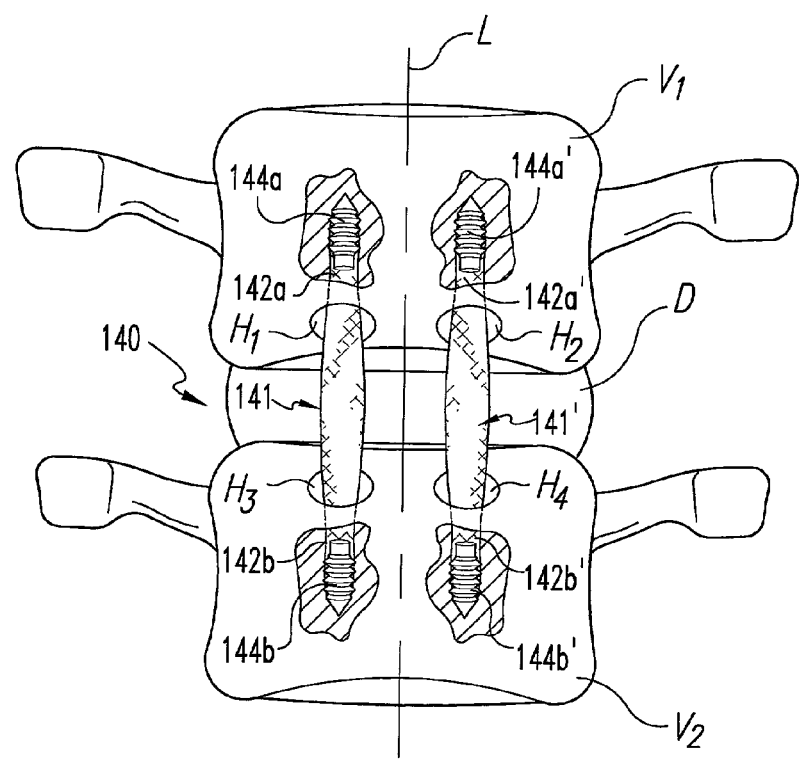
FIG. 16 is an anterior elevational view in partial section of a spinal column segment having another embodiment spine stabilization system attached thereto.
Figure 17:
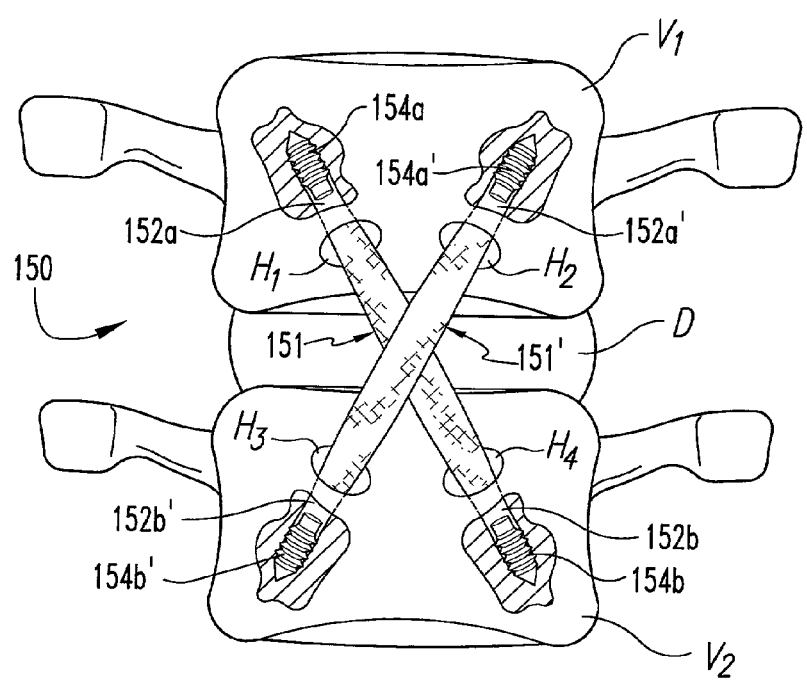
FIG. 17 is an anterior elevational view in partial section of a spinal column segment having another embodiment spine stabilization system attached thereto.

Referring now to FIGS. 16 and 17, further embodiments of spine stabilization systems are illustrated that employ multiple implants attached to vertebra V1 and V2. In FIG. 16 stabilization system 140 includes a first implant 141 offset laterally to a first side of the sagittal plane L, and a second implant 141' offset to a second side of the sagittal plane L. First and second implants 141, 141' can be equally spaced the same distance from plane L.

First implant 141 has a first end 142a extending through opening H1 and into a first tunnel formed in vertebra V1. First end 142a is attached to vertebra V1 with anchor 144a in the first tunnel. Implant 141 has an opposite second end 142b extending through opening H3 and into a third tunnel formed in vertebra V2. Second end 142b is attached to vertebra V2 with anchor 144b in the third tunnel.

Second implant 141' has a first end 142a' extending through opening H2 and into a second tunnel in vertebra V1. First end 142a' is attached to vertebra V1 with anchor 144a' in the second tunnel. Implant 141' has an opposite second end 142b' extending through opening H4 and into a fourth tunnel in vertebra V2. Second end 142b' is attached to vertebra V2 with anchor 144b' in the fourth tunnel.

In FIG. 17 stabilization system 150 is secured anteriorly to vertebrae V1 and V2. System 150 has a first implant 151 with a first end 152a extending through opening H1 and into a first tunnel formed in vertebra V1. First end 152a is attached to vertebra V1 with anchor 154a in the first tunnel. Implant 151 has an opposite second end 152b extending across sagittal plane L and through opening H4 and into a fourth tunnel formed in vertebra V2. Second end 152b is attached to vertebra V2 with anchor 154b in the fourth tunnel.

Stabilization system 150 has a second implant 151' with a first end 152a' extending through opening H2 and into a second tunnel formed in vertebra V1. First end 152a' is attached to vertebra V1 with anchor 154a' in the second tunnel. Implant 151' has an opposite second end 152b' extending through opening H3 and into a third tunnel formed in vertebra V2. Second end 152b' is attached to vertebra V2 with anchor 154b' in the third tunnel. Second implant 151' extends obliquely across sagittal plane L, forming an "X" shape with first implant 151. The angle of each implant 151, 151' relative to the sagittal plane may vary in the range from about 5 degrees to about 86 degrees, from about 20 degrees to about 70 degrees, and from about 30 degrees to about 60 degrees. The criss-crossing of implants 151, 151' improves the resistance of spinal stabilization system 150 to relative rotation or lateral bending between vertebrae V1 and V2.

Figure 18:
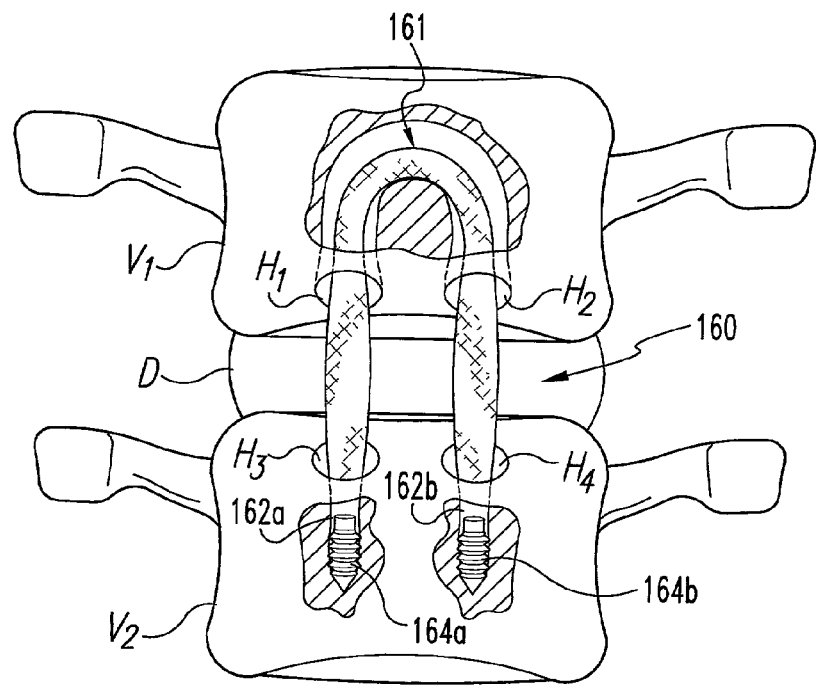
FIG. 18 is an anterior elevational view in partial section of a spinal column segment having another embodiment spine stabilization system attached thereto.

Referring now to FIG. 18 there is illustrated another embodiment of spinal stabilization system 160 attached to vertebrae V1 and V2. System 160 has an implant 161 bendable or flexible to assume a U-shaped configuration, and is attachable to the anterior, antero-lateral or lateral faces of vertebrae V1 and V2. A curved or non-linear tunnel is formed in vertebra V1 between openings H1 and H2 in the anterior face of vertebra V1. Vertebra V2 has formed therein a first tunnel extending from opening H3, and a second tunnel extending from opening H4. Implant 161 extends through the curved tunnel of vertebra V1, and has a first end 162a secured in the tunnel extending from opening H3 with first anchor 164a. Implant 161 has a second end 162b secured in the tunnel extending from opening H4 with second anchor 164b.

Figure 19:
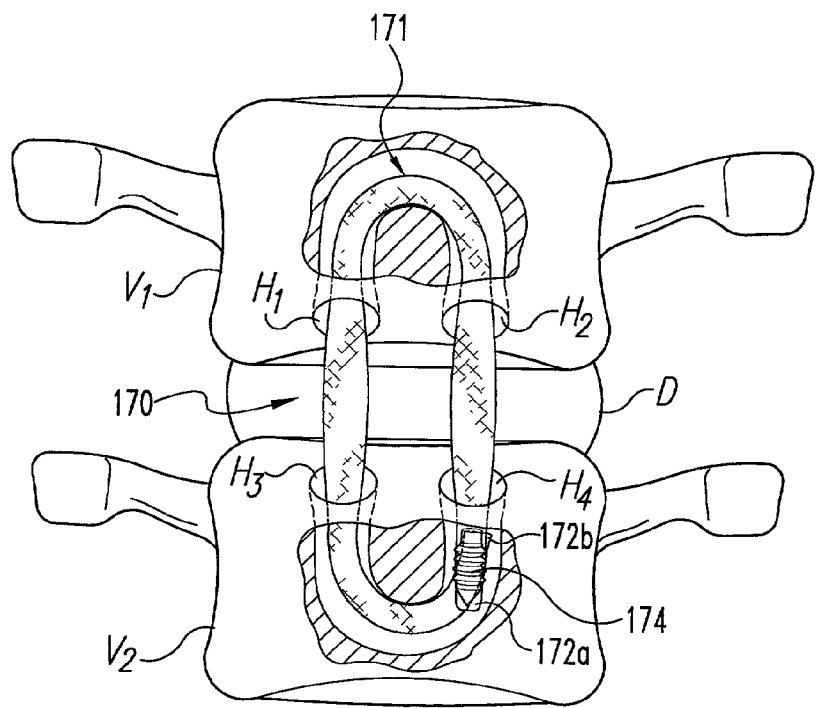
FIG. 19 is an anterior elevational view in partial section of a spinal column segment having another embodiment spine stabilization system attached thereto.

Referring now to FIG. 19 there is illustrated another spinal stabilization system 170 attached to vertebrae V1 and V2. System 170 has an implant 171 bendable or flexible to assume an oval-shaped configuration, and is attachable to the anterior, antero-lateral or lateral faces of vertebrae V1 and V2. A first curved or non-linear tunnel is formed in vertebra V1 between openings H1 and H2 in the anterior face of vertebra V1. A second curved or nonlinear tunnel is formed in vertebra V2 between openings H3 and H4 in the anterior face of vertebra V2. Implant 171 extends through the first tunnel of vertebra V1, and has a first end 172a positioned in the second tunnel of vertebra V2. Implant 171 has a second end 172b positioned in the second tunnel adjacent to or in overlapping arrangement with first end 172a. An anchor 174 secures ends 172a, 172b in the second tunnel of vertebra V2.

Figure 20:
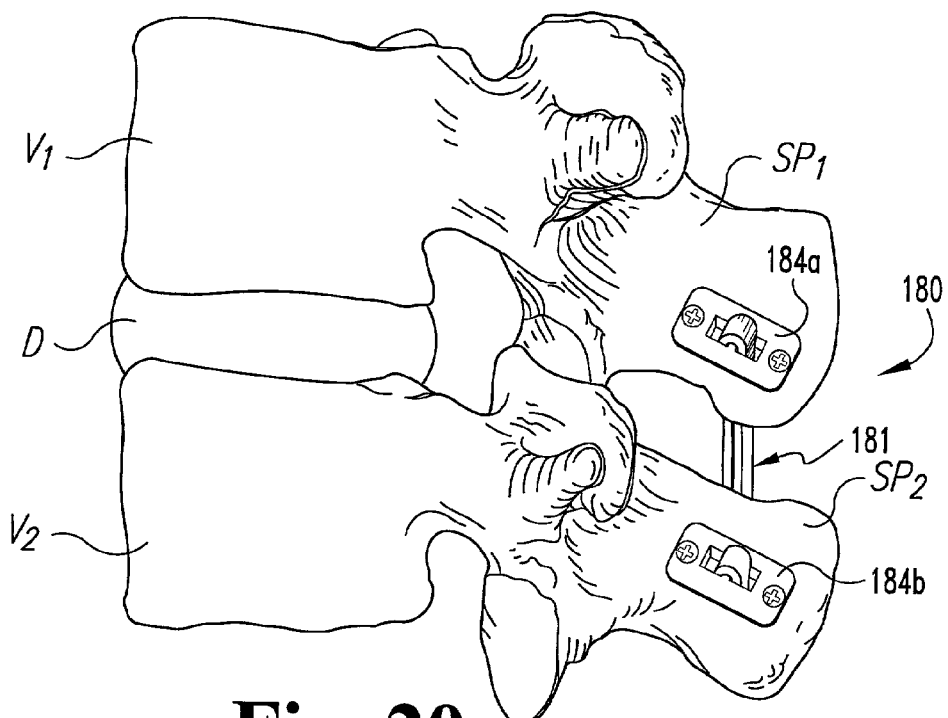
FIG. 20 is a side elevational view of a spinal column segment having a posterior spine stabilization system attached thereto.

Referring now to FIG. 20, there is shown another embodiment stabilization system 180 secured to the posterior portion of the spine. System 180 has an implant 181 that extends between and is attached to the spinous processes SP1 and SP2 of vertebrae V1 and V2 with anchors 184a and 184b, respectively. Anchors 184a and 184b are illustrated as buttons or buckles such as described above with respect to button 54. Tunnels can be drilled through each of the spinous processes SP1, SP2 sized to receive the ends of implant 181 therethrough for attachment to anchors 184a, 184b. Alternatively, the tunnels through SP1 and SP2 can be sized to receive an attachment loop or member extending from respective ones of the anchors 184a, 184b for engagement of the ends of implant 181 between SP1 and SP2.

Figure 21:
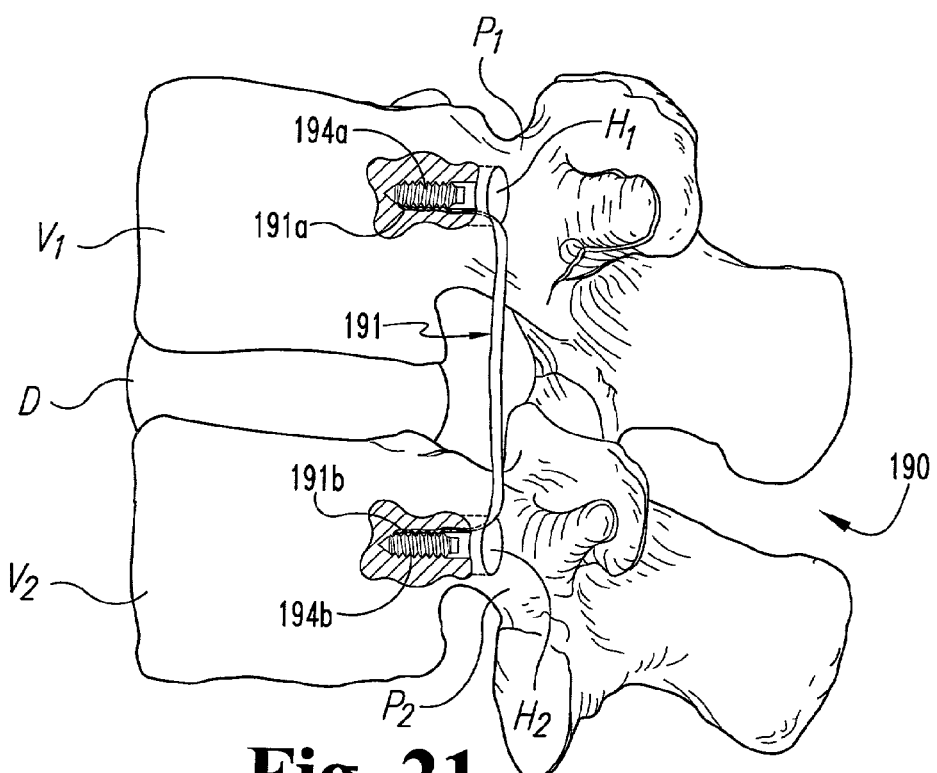
FIG. 21 is a side elevational view of a spinal column segment having another embodiment posterior spine stabilization system attached thereto.

In FIG. 21, another embodiment posterior spine stabilization system 190 is illustrated. Vertebra V1 includes a first tunnel formed in a pedicle thereof opening at H1 on the pedicle at the posterior portion of the spinal column segment. Vertebra V2 includes a second tunnel formed in or through a pedicle thereof and opening at H2 on the pedicle at the posterior portion of the spinal column segment. System 190 includes an implant 191 extending between and attached to the pedicles P1 and P2 of vertebrae V1 and V2. Implant 191 includes a first end 191a embedded in the first tunnel in vertebra V1 and attached thereto with anchor 194a. Implant 191 includes a second end 191b embedded in the second tunnel in vertebra V2 and attached thereto with anchor 194b. Anchors 194a and 194b are illustrated as threaded interference screws. However, other embodiments contemplate the use of other anchors described herein. Other embodiments also contemplate the attachment of posterior spine stabilization devices to the facets, pars, or transverse processes of vertebrae V1 and V2.

Figure 22:
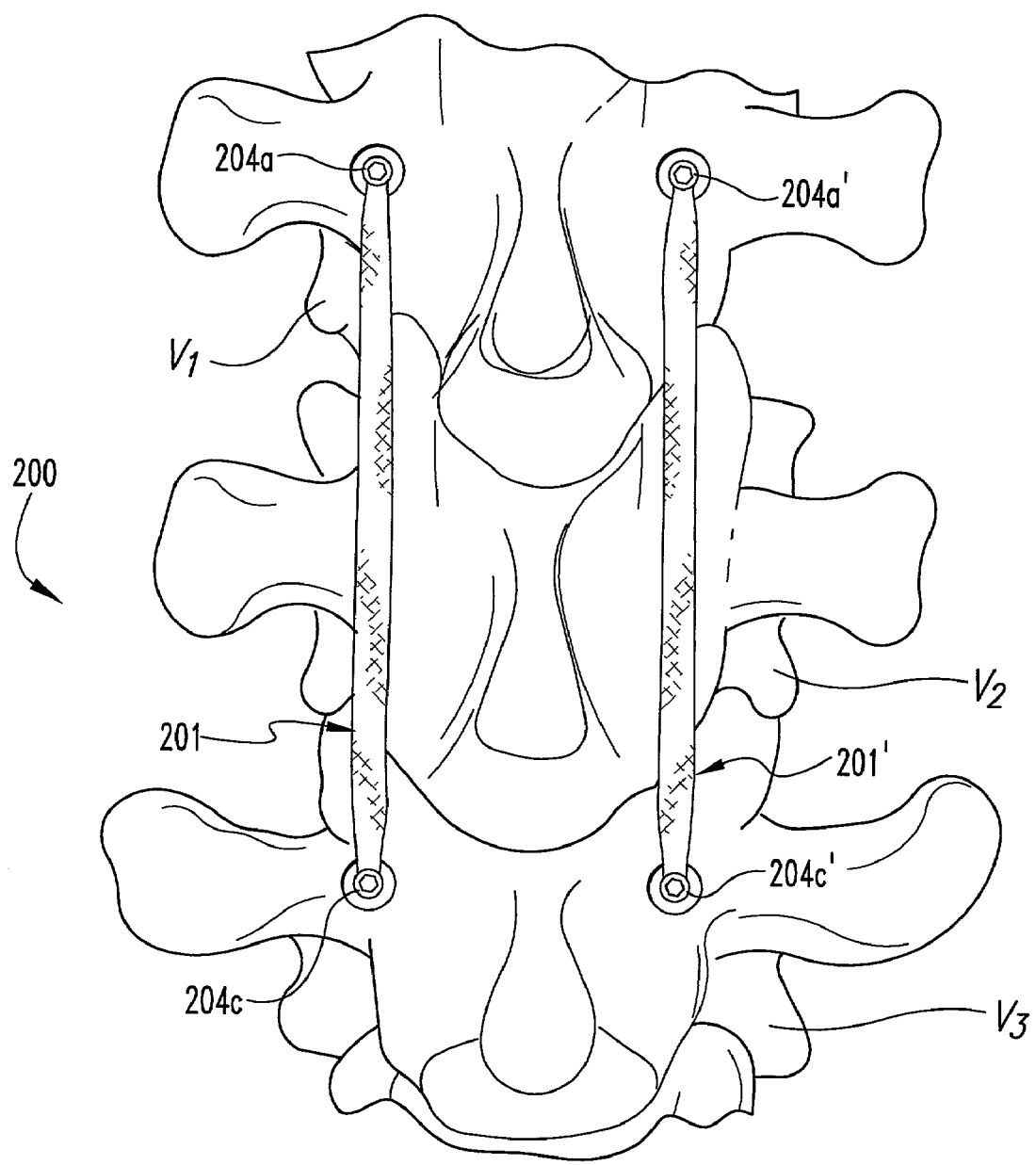
FIG. 22 is a posterior elevational view of a spinal column segment having another embodiment posterior spine stabilization device attached thereto.

Referring now to FIG. 22, a posterior view is provided of the posterior portion of the spinal column segment with a spine stabilization system 200 attached thereto along multiple levels. System 200 is similar to system 190 described above, and includes a first implant 201 attached to the pedicles of vertebrae V1 and V3 via anchors 204a and 204c, respectively, along one side of the spinous processes. The ends of implants 201 and anchors 204a, 204c can be embedded or positioned in tunnels formed in the pedicles of vertebra V1, V3. Spine stabilization system 200 further includes a second implant 200' attached to the pedicles of vertebrae V1 and V3 via anchors 204a' and 204c', respectively, along the other side of the spinous processes opposite implant 200. The ends of implant 201' and anchors 204a', 204c' can be embedded or positioned in tunnels formed in the pedicles of vertebra V1, V3. Implants 201, 201' can span across vertebra V2, or can be attached thereto with an anchor extending through or coupled to the implant.

The present invention further contemplates surgical methods for attaching a spinal stabilization system to first and second vertebrae. The openings and tunnels can be formed by drilling, tapping, chiseling, punching, or otherwise cutting the vertebral bodies. In the embodiments of the stabilization system employing curved or non-linear tunnels through the vertebrae, it is contemplated that a flexible drill can be used to create these curved tunnels. It is further contemplated that attachment of the stabilization systems could occur before, after or during placement of a device into the disc space between the first and second vertebrae.

In one specific application, the stabilization system is used to reconstruct the anterior longitudinal ligament. In one specific surgical technique, the disc space is accessed from an anterior approach and a fusion device, artificial disc or spacer is inserted into the disc space. A first opening and tunnel is formed into the upper vertebral body and a second opening and tunnel is formed into the lower vertebral body. One end of the implant is inserted into either the first or second tunnel, and the implant is attached to the corresponding vertebra with an anchor. The opposite end of the implant is inserted into the other tunnel formed in the other vertebra and attached with an anchor. A desired tension can be applied to the implant before attachment of the other end to the other vertebra. The applied tension may differ depending on whether the device inserted into the disc space is a fusion cages, an artificial disc, or spacer. The other end of the implant is then attached to the other vertebra using a second anchor. The anchors can be embedded in the vertebrae to reduce the profile of the system along the upper and lower vertebrae.

While the invention has been illustrated and described in detail in the drawings and foregoing description, the same is to be considered as illustrative and not restrictive in character, it being understood that only the illustrated embodiments have been shown and described, and that all changes and modifications that come within the spirit of the invention are desired to be protected. For example, the spine stabilization system could be employed across multiple vertebral levels. In another example, multiple spine stabilization systems could be employed on the same vertebral level such as across the anterior aspects and the lateral aspects of the same vertebrae.

What is claimed is:

1. A spine stabilization system, comprising:
    an implant having a first end and an opposite second end, at least a portion of one of said first and second ends structure for positioning in use in a tunnel formed in a first vertebral body; and
    at least one anchor securing the at least a portion of one of the first and second ends of the implant against being pulled from the tunnel within the first vertebral body without protruding from the first vertebral body for attaching said at least a portion of said one of said first and second ends of said implant to the first vertebral body when positioned in the tunnel with said implant including a body having a length and structure to extend from the tunnel along an outer surface of the first vertebral body to a second vertebral body.

2. The system of claim 1, wherein said at least one anchor extends along and threadingly engages said one of said first and second ends of said implant.

3. The system of claim 1, wherein the other of said first and second ends of said implant is structured for positioning in a second tunnel formed in the second vertebral body and further comprising a second anchor engageable to the second vertebral body for attaching said implant to the second vertebral body.

4. The system of claim 3, further comprising a device positionable in a spinal disc space between the first vertebral body and the second vertebral body.

5. The system of claim 1, wherein the tunnel forms an angle relative to an axial plane of the spinal column in the range of 0 degrees to 80 degrees.

6. The system of claim 5, wherein said angle is in the range of about 25 degrees to about 65 degrees.

7. The system of claim 1, wherein said at least one anchor is selected from the group consisting of: an interference screw, a suture anchor, a button, a spiked washer, and a pin fastener.

8. The system of claim 3, wherein said implant is flexible.

9. The system of claim 8, wherein said implant extends along the anterior faces of the first vertebral body and the second vertebral body when attached thereto.

10. The system of claim 8, wherein said implant extends along the lateral faces of the first vertebral body and the second vertebral body when attached thereto.

11. The system of claim 8, wherein said implant extends between a pedicle of the first vertebral body and a pedicle of the second vertebral body when attached thereto.

12. The system of claim 8, wherein said implant comprises a synthetic resorbable material selected from the group consisting of: polylactide, polyglycolide, tyrosine-derived polycarbonate, polyanhydride, polyorthoester, polyphosphazene, calcium phosphate, hydroxyapatite, bioactive glass and combinations thereof.

13. The system of claim 8, wherein said implant comprises a natural resorbable material selected from the group consisting of: autograft, allograft, xenograft, soft tissues, connective tissues, demineralized bone matrix, and combinations thereof.

14. The system of claim 8, wherein said implant comprises a nonresorbable material selected from the group consisting of: polyethylene, polyester, polyvinyl alcohol, polyacrylonitrile, polyamide, polytetrafluorethylene, polyparaphenylene terephthalamide, cellulose, shape-memory alloys, titanium, titanium alloys, stainless steel, and combinations thereof.

15. The system of claim 1, wherein said at least one anchor is positionable in a second tunnel that intersects the tunnel in which said one end of said implant is positioned.

16. The system of claim 15, wherein the tunnel extends from an anterior face of the first vertebral body and the second tunnel extends from a lateral face of the first vertebral body.

17. The system of claim 15, wherein the tunnel extends from an anterior face of the first vertebral body and the second tunnel extends from an antero-lateral face of the first vertebral body.

18. The system of claim 17, wherein the tunnel is curved toward the second tunnel and the second tunnel extends obliquely relative to the saggital plane.

19. The system of claim 15, wherein:
    the tunnel extends from an anterior face of the first vertebral body adjacent one vertebral endplate at a first angle relative to the axial plane of the spinal column; and
    the second tunnel extends from the anterior face of the first vertebral body adjacent the other endplate at a second angle relative to the axial plane of the spinal column.

20. The system of claim 19, wherein said first angle and said second angle are equal.

21. The system of claim 1, wherein:
the tunnel extends through the first vertebral body from a first opening adjacent one endplate of the first vertebral body to a second opening adjacent the other endplate of the first vertebral body; and
said one end of said implant is positionable from the first opening through the tunnel and for attachment to the first vertebral body at the second opening with said at least one anchor.

22. The system of claim 21, wherein said first opening opens at the one vertebral endplate.

23. The system of claim 1, further comprising:
a second implant having a first end and an opposite second end, at least a portion of said first and second ends of the second implant being positionable in a second tunnel formed in the first vertebral body; and
a second anchor engageable to the first vertebral body for attaching said second implant to the first vertebral body.

24. The system of claim 23, wherein:
said implant is attachable along the anterior face of the first vertebral body on one side of the sagittal plane; and
said second implant is attachable along the anterior face of the first vertebral body on the other side of the sagittal plane.

25. The system of claim 23, wherein:
at least a portion of the other of said first and second ends of said implant is positionable in a third tunnel formed in a second vertebral body and further comprising a third anchor for attaching said implant to the second vertebra; and
at least a portion of the other of said first and second ends of said second implant is positionable in a fourth tunnel formed in the second vertebral body and further comprising a fourth anchor for attaching said second implant to the second vertebra.

26. The system of claim 25, wherein said implant and said second implant are parallel to one another.

27. The system of claim 25, wherein said implant and said second implant cross over one another.

28. The system of claim 25, wherein each of said at least one anchor, said second anchor, said third anchor and said fourth anchor are interference screws positionable in respective ones of the tunnel, the second tunnel, the third tunnel, and the fourth tunnel in engagement with the respective ends of said implant and said second implant.

29. The system of claim 1, further comprising:
a second tunnel formed in the first vertebral body and spaced from the tunnel;
a third tunnel extending through a second vertebral body from a first opening adjacent one endplate of the second vertebral body to a second opening adjacent the one endplate of the second vertebral body, wherein said implant is positionable through the third tunnel and at least a portion of the other of said first and second ends is positionable in the second tunnel, and further comprising a second anchor engageable to the first vertebral body for attaching said other end of said implant to the first vertebral body.

30. The system of claim 1, wherein the tunnel extends between a first opening adjacent an endplate of the first vertebral body and a second opening adjacent the endplate of the first vertebral body, and further comprising a second tunnel extending through a second vertebral body from a third opening adjacent one endplate of the second vertebral body to a fourth opening adjacent the one endplate of the second vertebral body, wherein said implant is positionable through the second tunnel and the other of said first and second ends is positionable into the first tunnel and overlaps said one end of said implant when attached to the first vertebral body.

31. The system of claim 1, wherein said at least one anchor extends along said one end of said implant.

32. The system of claim 1, wherein said at least one anchor intersects said one end of said implant.

33. The system of claim 1, wherein said at least one anchor is attached to said one end of said implant.

34. The system of claim 1, further comprising a second tunnel formed in the first vertebral body spaced from the tunnel, and wherein said one end of said implant has a second portion positionable in the second tunnel and attached thereto with a second anchor engaged to the first vertebral body.

35. The system of claim 1, wherein said implant comprises a substantially inelastic material.

36. The system of claim 1, wherein said implant comprises a substantially flexible material.

37. A spine stabilization system, comprising:
an implant having a first end and an opposite second end, at least one of said first and second ends being positionable in a tunnel formed in a first vertebral body; and
at least one anchor securing the at least one of the first and second ends of the implant against being pulled from the tunnel within the first vertebral body without protruding from the first vertebral body, wherein said implant includes a portion between said first and second ends sized to extend from the first vertebral body to a second vertebral body, said one of said first and second ends and said portion of said implant are flexible and angled relative to one another and said portion includes a length sized to extend from the first vertebral body toward the second vertebral body with the one of the first and second ends and said portion being structured to conform to an outer surface of the vertebral body when oriented for positioning into the first vertebral body in the tunnel.

38. The system of claim 37, wherein said at least one anchor is sized to not protrude from the first vertebral body when in engagement with said one of said first and second ends.

39. The system of claim 37, wherein the other of said first and second ends of said implant is positionable in a second tunnel formed in the second vertebral body and further comprising a second anchor engageable to the second vertebral body in the tunnel for attaching said implant to the second vertebral body, wherein said at least one anchor and said second anchor are each sized to not protrude from the respective vertebral bodies when positioned therein in engagement with said implant.

40. The system of claim 39, wherein the first and second ends extend in opposite directions from one another and are angled relative to said portion such that when engaged to the respective vertebral bodies the first and second ends each form an angle ranging from about 0 degrees to about 80 degrees relative to an axial plane taken at an entry location of the respective first and second ends into the respective vertebral body.

41. The system of claim 40, wherein said angles are in the range of about 25 degrees to about 65 degrees.

42. The system of claim 39, further comprising a device positionable in a spinal disc space between the first vertebral body and the second vertebral body.

43. The system of claim 39, wherein said at least one anchor is selected from the group consisting of: an interference screw, a suture anchor, a button, a spiked washer, and a pin fastener.

44. The system of claim 39, wherein said implant is flexible.

45. The system of claim 44, wherein said implant extends along and is conformable to anterior faces of the first vertebral body and the second vertebral body when positioned in the tunnels.

46. The system of claim 37, wherein said at least one anchor extends along said one of said first and second ends of said implant when engaged thereto.

47. The system of claim 37, wherein said at least one anchor is attached to said one of said first and second ends of said implant.

48. The system of claim 37, wherein said implant comprises a substantially inelastic material.

49. The system of claim 37, wherein said implant comprises a substantially flexible material.

50. The system of claim 37, wherein said at least one anchor extends along and threadingly engages said one of said first and second ends of said implant.

51. A spine stabilization system, comprising:
an implant having a flexible, conformable body extending between a first end and an opposite second end, at least a portion of one of said first and second ends including means for conforming to a first vertebral body in a tunnel formed in a first vertebral body; and
at least one anchor securing the at least a portion of one of the first and second ends of the implant against being pulled from the tunnel within the first vertebral body in without protruding from the first vertebral body, said at least one anchor and said one of said first and second ends being configured to engage one another in the tunnel with said means for conforming further having a length extending from the tunnel to conform to an outer surface of the first vertebral body outside the tunnel.

52. The system of claim 51, wherein said one of said first and second ends and said at least one anchor form an acute angle relative to an axial plane of the spinal column when engaged to the first vertebral body, wherein said angle is in the range of about 25 degrees to about 65 degrees.

53. The system of claim 51, wherein the other of said first and second ends of said implant is positionable in a second tunnel formed in a second vertebral body and further comprising a second anchor engageable to the second vertebral body for attaching said implant to the second vertebral body.

54. The system of claim 53, wherein when in the respective tunnels each of said first and second ends of said implant extends in a direction opposite one another and at an acute angle relative to an axial plane of the spinal column taken between the vertebral bodies.

55. The system of claim 54, wherein the angle of the first and second ends relative to the axial plane is in the range from about 25 degrees to about 65 degrees.

56. The system of claim 53, further comprising a device positionable in a spinal disc space between the first vertebral body and the second vertebral body.

57. The system of claim 53, wherein said body is structured for positioning on anterior faces of the first vertebral body and the second vertebral body when said first and second ends are positioned in respective ones of said tunnels.

58. The system of claim 51, wherein said at least one anchor extends along and threadingly engages said one of said first and second ends of said implant.

* * * * *